United States Patent [19]

Beuscher et al.

[11] Patent Number: 5,489,585
[45] Date of Patent: Feb. 6, 1996

[54] ALKOXYLATED PHENYL AND COUMARIN DERIVATIVES USEFUL IN THE TREATMENT OF VIRAL INFECTIONS

[75] Inventors: Norbert Beuscher, Salzgitter; Helmut Ritter, Wuppertal; Cornelia Bodinet, Salzgitter, all of Germany

[73] Assignee: Schaper & Bruemmer GmbH & Co., KG, Salzgitter, Germany

[21] Appl. No.: 972,021

[22] Filed: Nov. 9, 1992

[30] Foreign Application Priority Data

Nov. 9, 1991 [DE] Germany ............. 41 36 900.9

[51] Int. Cl.$^6$ ............................................. A61K 31/35
[52] U.S. Cl. ............................................. 514/457
[58] Field of Search ................................ 514/457

[56] References Cited

U.S. PATENT DOCUMENTS

| | | | |
|---|---|---|---|
| 3,983,164 | 9/1976 | Thorne et al. | 260/473 |
| 4,067,892 | 1/1978 | Thorne et al. | 260/410.9 |
| 4,098,816 | 7/1978 | Thorne et al. | 260/520 |
| 5,100,914 | 3/1992 | Rendenbal-Mueller et al. | 514/457 |

FOREIGN PATENT DOCUMENTS

| | | |
|---|---|---|
| 0124363 | 11/1984 | European Pat. Off. . |
| 0282179 | 9/1988 | European Pat. Off. . |
| 0697515 | 11/1979 | U.S.S.R. ............. A61K 31/57 |

OTHER PUBLICATIONS

Compernolle et al. 87CA:200294g 1977.

*Primary Examiner*—Russell Travers
*Attorney, Agent, or Firm*—Foley & Lardner

[57] ABSTRACT

Alkoxylated phenyl and coumarin derivatives useful in the treatment of viral infections are disclosed. The compounds are particularly useful in the treatment of picornaviruses, and more particularly in the treatment of rhinoviruses.

7 Claims, No Drawings

ALKOXYLATED PHENYL AND COUMARIN DERIVATIVES USEFUL IN THE TREATMENT OF VIRAL INFECTIONS

BACKGROUND OF THE INVENTION

The present invention relates to alkoxylated phenyl and coumarin derivatives useful in the treatment of viral infections, particularly influenza and acute rhinitis.

In humans, picornaviruses cause a number of syndromes of differing degree of severity. These include life-threatening infections such as poliomyelitis, hepatitis A and influenza and minor infections, such as the cold. This is often caused by rhinoviruses, of which at the present time over 100 serotypes are known.

To date, numerous substances have been developed which have a certain activity against rhinoviruses. The structures and properties of such compounds are presented in various papers, for example in M. S. Chapman et al., *J. Mol. Biol.*, 217:455–463 (1991). A few of the compounds, for example, an oxazolinylisoxazole or a phosphorylated chalcone derivative or 4,6'-dichloroflavan have an excellent activity in vitro. Therapeutic use unfortunately has not been successful, however, either because of lack of activity in vivo or because of serious side effects, for example, severe irritation of the mucosal membranes in the nose (cf. P. G. Higgens et al., *The British Soc. for Antimicrobial Chemotherapy*, (1984), 403–409).

Also worthy of note is an observation by G. D. Diana et al. (*J. Med. Chem.*, 28:1906–1910 (1985)) that isoxazole derivatives have a certain antiviral activity, for example, against rhinoviruses. Substances containing these isoxazoles have not been used therapeutically.

SUMMARY OF THE INVENTION

It is therefore an object of the present invention to provide a composition effective in the treatment of infections caused by picornaviruses, particularly rhinoviruses, and more particularly influenza and acute rhinitis.

It is a further object of the present invention to provide a method for treating infections caused by picornaviruses, particularly rhinoviruses, and more particularly influenza and acute rhinitis.

These and other objects according to the invention are provided by a method of treating a subject infected with a pacornavirus, comprising the step of administering an antiviral effective amount of a pharmaceutical composition comprising an alkoxylated phenyl or coumarin derivative according to forumla I $$R^1\text{-}X\text{-}R^2 \quad (I)$$

wherein
X has from 2 to 12 carbon atoms and is an aliphatic group, a heteroaliphatic group having 1 to 2 oxygen atoms or a cycloaliphatic group,
$R^1$ is represented by one of the formulae Ia or Ib

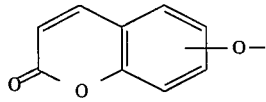
(Ia)

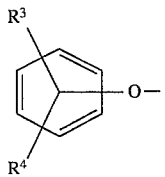
(Ib)

wherein
$R^3$ is hydrogen, hydroxy, alkoxy, or a carboxylic acid derivative,
$R^4$ represents a carboxylic acid group, an alkylcarboxylic acid group, an acrylic group or a derivative of one of these groups, and
$R^2$ is the same as $R^1$ or is one of hydroxy, bromide, chloride, alkoxycarbonyl having from 1 to 6 carbon atoms, optionally-substituted amino and oxyphenyl of the formula Ic

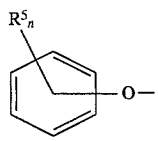
(Ic)

wherein
$R^5$ is alkyl or oxyalkyl, and
m is an integer between 1 and 5, and a pharmaceutically acceptable excipient.

In accordance with another aspect of the present invention, there is provided a pharmaceutical composition comprising:
an alkoxylated phenyl or coumarin derivative according to forumla II $$R^6\text{-}X\text{-}R^7 \quad (II)$$

wherein
X has from 2 to 12 carbon atoms and is an aliphatic group, a heteroaliphatic group having 1 to 2 oxygen atoms or a cycloaliphatic group,
$R^6$ is represented by one of the formulae (IIa) or (IIb)

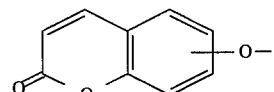
(IIa)

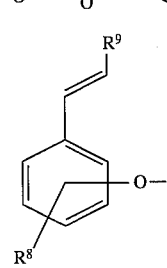
(IIb)

wherein
$R^8$ is hydrogen, hydroxy, alkoxy, or a carboxylic acid derivative,
$R^9$ represents a carboxylic acid group, an alkylcarboxylic acid group, or a derivative of one of these groups, and
$R^7$ is the same as $R^6$ or is one of hydroxy, bromide, chloride, alkoxycarbonyl having from 1 to 6 carbon atoms, optionally-substituted amino and oxyphenyl of the formula (IIc)

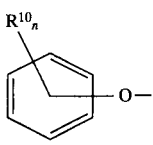

wherein
R$^{10}$ is alkyl or oxyalkyl, and
m is an integer between 1 and 5, and a pharmaceutically acceptable excipient.

Further objects, features, and advantages of the present invention will become apparent from the detailed description of preferred embodiments that follows.

DETAILED DESCRIPTION OF THE PREFERRED EMBODIMENTS

Alkoxylated phenyl or coumarin derivatives according to the present invention are represented by the formula (I)

in which X has 2 to 12 carbon atoms and is an aliphatic group, a heteroaliphatic group having 1 to 2 O atoms or a cycloaliphatic group, and R$^1$ is described by the formulae

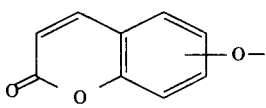

or

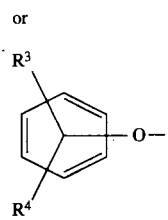

where R$^3$ represents hydrogen, a hydroxy or alkoxy group or a carboxylic acid derivative, R$^4$ represents a carboxylic acid, alkylcarboxylic acid or acrylic acid function or a derivative thereof such as an amide or ester, and R$^2$ represents a radical from the group R$^1$, a hydroxy group, bromide, chloride, alkoxycarbonyl having 1 to 6 C atoms, an unsubstituted or substituted amino function or a phenoxy radical of the formula (Ic)

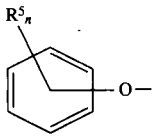

where m is an integer between 1 and 5 and R$^5$ represents an alkyl or alkoxy radical. They are used in preparation of a medicament for the treatment of virus infections, in particular influenza and acute rhinitis.

Compounds of formula II are especially useful in a medicment.

When R$^2$ in formula I or R$^7$ in formula II is an amino radical it is preferably N-piperidyl, N-morpholyl, N-diethanolamino, N-alkyl-N-ethanolamine or N-dialkyl.

R$^4$ or R$^9$ may be a derivative of a carboxylic acid, alkylcarboxylic acid or acrylic acid, for example, an amide or an ester. For example, R$^4$ or R$^9$ may be carboxamide, alkylcarboxamide or acrylamide, preferably having an aliphatic or cycloaliphatic substituent, with cyclohexyl being the preferred cycloaliphatic substituent.

R$^4$ or R$^9$ may also be a carboxylic acid alkyl ester, an alkyl carboxylic acid alkyl ester or an acrylic acid alkyl ester, preferably one that has from 1 to 10 carbon atoms. Alternatively, R$^4$ or R$^9$ may be a carboxylic acid cylcoalkyl ester, an alkyl carboxylic acid cylcoalkyl ester or an acrylic acid cycloalkyl ester. Cyclohexyl is preferred as the cycloalkyl group in this case.

The alkoxylated phenyl and coumarin derivatives of the formula (I) and (II) are used in the preparation of medicaments for the therapeutic treatment of infections caused by picorna viruses, in particular for the control of virus diseases which have been induced by rhinoviruses.

The substances according to formula (I) and (II) can be pharmaceutically formulated in a customary manner and administered orally, intravenously, intramuscularly or topically. In this connection, customary methods of administration are suitable, such as, for example, tablets, capsules, coated tablets, syrups, solutions, suspensions, sprays or ointments. When the substance is to be injected, water is preferably used as the injection medium and may contain the additives customary in injection solutions, such as stabilizers, solubilizers and buffers. Additives of this type are, for example, tartrate and citrate buffers, ethanol, complexing agents such as ethylenediaminetetraacetic acid and its non-toxic salts, as well as high-molecular weight polymers, such as liquid polyethylene oxide, for viscosity regulation. Liquid excipients for injection solutions must be sterile and are preferably filled intoampoules. Solid excipients are, for example, starch, lactose, mannitol, methylcellulose, talc, highly disperse silica, relatively high-molecular weight fatty acids such as stearic acid, gelatin, agar-agar, calcium phosphate, magnesium stearate, animal and vegetable fats, solid high-molecular weight polymers such as polyethylene glycols and other chemical compounds.

Cyclodextrin inclusion compounds which lead to an improved solubility of the compounds in aqueous medium can also be prepared by known methods from the inventive compounds. In addition to unmodified cyclodextrins, alkylated cyclodextrin derivatives, such as, for example, dimethyl-β-cyclodextrin, are particularly suitable.

The dosage may depend on various factors, such as the manner of administration, species, age or condition of the individual. The compounds according to the invention are customarily administered in amounts from about 0.1 to about 100 mg, preferably about 0.2 to about 80 mg per day and per kilogram of body weight. It is preferred to divide the daily dose into two to five administrations, one or two tablets having an active compound content from about 0.5 to about 500 mg being administered on each administration. The tablets can also be of the sustained-release type, by means of which the number of administrations per day decreases to one to three. The active compound content of the sustained-release tablets can be about 2 to about 1000 mg. The active compound can also be given by continuous infusion, amounts from about 5 to about 1000 mg per day normally being sufficient. On topical application, the compound can be administered up to five times daily, preferably in an amount from about 0.1 to about 50 mg.

Synthesis of compounds according to the invention is readily carried out by methods known to the person skilled in the art. The following examples exemplify preparation of the compounds.

SYNTHESIS EXAMPLE 1

Hexamethylenebis(7-oxycoumarin)

An amount of 8.92 g (55 mmol) of umbelliferone (7-hydroxycoumarin) and 7.60 g (55 mmol) of K$_2$CO$_3$ are suspended in 250 ml of acetone and 6.10 g (25 mmol) of hexamethylene dibromide are then added. The reaction mixture is heated under reflux for 30 hours. During this time, the suspension becomes increasingly mobile. After cooling to room temperature, the reaction mixture is poured into 300 ml of water and rendered acidic with dilute hydrochloric acid. The solid residue is filtered off with suction and washed with water. The crude product is stirred with 100 ml of ethanol and the crystals are filtered off with suction again. The colorless product is finally dried over $P_4O_{10}$ in vacuo.

Yield: 5.6 g (55%).

Melting point: 162°–163° C.

IR (KBr): 3050, 3045 (CH, aromatic); 2940, 2905, 2870 (CH, aliphatic); 1715 (C═O) 1620 (C═C) 1605 (aromatic C═C), in each case in $cm^{-1}$.

H-NMR ($CDCl_3$, 250 MHz); 1.55 m (4H); 1.84 m (4H), 4.01 t (4H), 6.21 d (2H), 6.75–1.83 m (4H), 7.34 d (2H), 7.61 d (2H), in each case in ppm.

SYNTHESIS EXAMPLE 2

Ethyl 4-(6-bromohexoxy)benzoate

An amount of 16.6 g (100 mmol) of ethyl 4-hydroxybenzoate, 122 g (500 mmol) of 1,6-dibromohexane, 10.0 g of $K_2CO_3$ (finely powdered in a mortar and dried) are heated under reflux in 75 ml of absolute acetone. After 20 hours, first the acetone and then the excess of dibromohexane are removed by distillation at 15 mmHg. The crude product is purified in a high vacuum by means of a bulb tube distillation apparatus. After recrystallization from a little ethanol and drying in vacuo over $P_4O_{10}$, about 10 g of analytically pure product are obtained. The melting point is in the room temperature range.

SYNTHESIS EXAMPLE 3

Ethyl 4-[6-(N-diethanolamino)hexoxy] benzoate

An amount of 3.29 g (1 mmol) of ethyl 4-(6-bromohexoxy)benzoate (cf. Synthesis Example 2) and 2.2 g (2.1 mmol) of diethanolamine are heated under reflux for 4 hours in 10 ml of nitromethane. The solvent is then removed by evaporation in vacuo. The residue is taken up in 40 ml of dichloromethane, the mixture is thoroughly shaken with water, and the organic phase is dried using $Na_2SO_4$, filtered and evaporated to dryness. The residue is covered with a little ether and petroleum ether. The final product crystallizes out at 0° C. in pure form. Melting point 18°–20° C.

Particularly preferred compounds according to the present invention are the following compounds:
Hexamethylenebis(ethyl 4-oxycinnamate)
Hexamethylenebis(methyl 4-oxycinnamate)
Hexamethylenebis(7-oxycoumarin)
Pentamethylenebis(ethyl 4-oxycinnamate)
Ethyl 4-[6-(4-toluoyloxy)hexoxy]benzoate
Ethyl 4-[6-(umbelliferyl)hexoxy]benzoate
Ethyl 4-(6-bromohexoxy)benzoate
Ethyl 4-[6-(N-diethanolamino)hexoxy]benzoate The antiviral action of the compounds according to the invention is illustrated by means of the examples that follow, but the invention is not restricted to these examples.

EXAMPLE 1

Rhinoviruses can be divided into two groups on the basis of the receptor to which they bind. A large group includes rhinovirus type 2, and a small group includes rhinovirus type 1A. The compounds according to the invention showed the following activity against rhinovirus type 2:

TABLE 1

|  | Concentration [µg/ml] | Plaque number |
|---|---|---|
| Control | — | 176 |
| Hexamethylenebis-(ethyl 4-oxybenzoate) | 25 | 0 |
| Octamethylenebis-(ethyl 4-oxybenzoate) | 25 | 21 |
| Hexamethylenebis-(ethyl 4-oxycinnamate) | 25 | 0 |
| Hexamethylenebis-(ethyl 4-oxycinnamate) | 12.5 | 0 |
| Hexamethylenebis-(ethyl 4-oxycinnamate) | 6.25 | 0 |

The compounds according to the invention showed the following activity against rhinovirus type 1A:

TABLE 2

|  | Concentration [µg/ml] | Plaque number |
|---|---|---|
| Control without substance | — | 168 |
| Hexamethylenebis-(ethyl 4-oxycinnamate) | 12.5 | 0 |
| Hexamethylenebis-(ethyl 4-oxycinnamate) | 6.25 | 47 |

The tolerability of the compounds according to the invention was tested in various mammalian cell lines. The following results (Table 3) were obtained here on Hela cells:

TABLE 3

|  | Non-toxic threshold concentration [µg/ml] |
|---|---|
| Control without substance | — |
| Trimethylenebis(ethyl 4-oxybenzoate) | 200 |
| Tetramethylenebis(ethyl 4-oxybenzoate) | 200 |
| Hexamethylenebis(ethyl 4-oxybenzoate) | 50 |
| Hexamethylenebis(ethyl 4-oxycinnamate) | 200 |
| Octamethylenebis(ethyl 4-oxybenzoate) | 25 |
| Ethyl 4-[6-(4-toluoyloxy)hexoxy]benzoate | 200 |
| Ethyl 4-[6-(umbelliferyl)hexoxy]benzoate | 50 |
| Ethyl 4-(6-bromohexoxy)benzoate | 100 |
| Ethyl 4-[6-(N-morpholyl)hexoxy]benzoate | 25 |
| Hexamethylenebis(7-oxycoumarin) | 200 |
| Ethyl 4-(6-diethanolaminohexoxy)benzoate | 12 |

The preferred substances thus have a very good tolerability in cell culture. This is in some cases considerably above the data published for 4'-ethoxy-2'-hydroxy- 4,6'-dimethylchalcone [cf. H. Ishitsuka et al. *Antimicrob. Agents and Chemotherapy* 22(4):617–621 (1982)].

The surprising antiviral activity of the active compounds according to the invention against rhinovirus type 2 can additionally be seen from Table 4. The selectivity index is in this case based on a 50% or 100% plaque reduction and results for SI 50% from the quotients of the highest non-cytotoxic concentration which causes an at least 50% plaque reduction, and the lowest non-cytotoxic concentration which causes an at least 50% plaque reduction. The same applies to SI 100% (Mohamed Abou-Karam, et al., *Journal of Natural Products*, Vol. 53, No. 2, pp. 340–344, March–April 1990). The abbreviation "n.d." in Table 4 means "not determinable."

TABLE 4

Antivital activity against rhinovirus type 2

| Test substance | "SI 50 %" | "SI 100 %" | Effective concentration range μg/ml |
|---|---|---|---|
| Umbelliferyl-hexoxy-(2-methylbenzene) | 4 | n.d. | 10–2.5 |
| Umbelliferyl-hexoxy-(4-benzonitrile | 4 | n.d. | 10–5 |
| Umbelliferyl-hexoxy-(2-nitrobenzene | 2 | 2 | 25–12.5 |
| Umbelliferyl-hexoxy-(4-propiophenone) | 8 | 2 | 50–6.25 |
| Umbelliferyl-hexoxy-(3,4-dimethylbenzene) | 8 | 4 | 10–1.3 |
| Umbelliferyl-hexoxy-(4-benzophenone | 2 | 1 | 1.25–0.5 |
| Umbelliferyl-hexyl bromide | 4 | 2 | 5–1.3 |
| Umbelliferyl-hexoxy-(4-nitrobenzene) | 2 | 1 | 2.5–1.3 |
| Umbelliferyl-hexoxy-(4-methylbenzene) | 2 | 1 | 2.5–1.3 |
| Umbelliferyl-hexoxy-(2-bromobenzene) | 2 | 1 | 2.5–1.3 |
| Umbelliferyl-hexoxybenzene | 2 | n.d. | 2.5–1.3 |
| Umbelliferyl-hexoxy-4-fluorobenzene | n.d. | n.d. | — |
| Umbelliferyl-hexoxy-(3-chloro-2-toluene | 2 | 1 | 50–25 |
| Umbelliferyl-hexoxy-4-chlorobenzene | 2 | n.d. | 12.5–6.25 |
| Umbelliferyl-hexoxy-3-anisole | 4 | 1 | 50–12.5 |
| Umbelliferyl-hexoxy-2-naphthalene | 8 | n.d. | 10–1.25 |
| Umbelliferyl-hexoxy-1-naphthalene | 2 | n.d. | 10–5 |
| Umbelliferyl-hexoxy-3-methylbenzene | n.d. | n.d. | — |
| Umbelliferyl-hexoxy-2,6-dimethylbenzene | 2 | 1 | 5–2.5 |

TABLE 4-continued

Antivital activity against rhinovirus type 2

| Test substance | "SI 50 %" | "SI 100 %" | Effective concentration range μg/ml |
|---|---|---|---|
| Umbelliferyl-hexoxyeugenol | 20 | 10 | 2.5–0.125 |
| m-Phenylenebis-(hexoxy-umbelliferone) | 2 | n.d. | 5–2.5 |
| Umbelliferyl-hexoxy-4-cinnamic acid | 4 | n.d. | 10–2.5 |

What is claimed is:

1. A method of treating a picornavirus infection in a subject infected with a picornavirus, comprising the step of administering an antiviral effective amount of a pharmaceutical composition comprising a coumarin derivative according to forumla I $$R^1\text{-}X\text{-}R^2 \tag{I}$$

wherein

X has from 2 to 12 carbon atoms and is an aliphatic group, $R^1$ is represented by the formula Ia

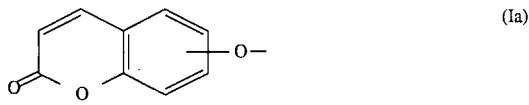
(Ia)

$R^2$ is the same as $R^1$ or is one of hydroxy, bromide, chloride, alkoxycarbonyl having from 1 to 6 carbon atoms, optionally-substituted amino and oxyphenyl of the formula Ic

(Ic)

wherein $R^5$ is alkyl or oxyalkyl, and m is an integer between 1 and 5, and a pharmaceutically acceptable excipient.

2. A method as recited in claim 1, wherein the composition is administered in an amount between about 0.1 and about 100 mg/day/kilogram body weight.

3. A method as recited in claim 1, wherein the composition is administered in an amount between about 0.2 and about 80 mg/day/kilogram body weight.

4. A method as recited in claim 1, wherein the composition is administered intravenously.

5. A method as recited in claim 1, wherein the composition is administered intramuscularly.

6. A method as recited in claim 1, wherein the composition is administered topically.

7. A method of treating a subject infected with a rhinovirus, comprising the step of administering a composition as recited in claim 1.

* * * * *

UNITED STATES PATENT AND TRADEMARK OFFICE
CERTIFICATE OF CORRECTION

PATENT NO. : 5,489,585
DATED : February 6, 1996
INVENTOR(S) : BEUSCHER et al.

It is certified that error appears in the above-indentified patent and that said Letters Patent is hereby corrected as shown below:

On the title page, under the Heading "FOREIGN PATENT DOCUMENTS", Please insert after the last entry the following:

24 39 458  02/75  Federal Republic of Germany.

89/07939  08/09/89  PCT/US.

3-227923  08/10/91  Japan.

UNITED STATES PATENT AND TRADEMARK OFFICE
CERTIFICATE OF CORRECTION

PATENT NO. : 5,489,585
DATED : February 6, 1996
INVENTOR(S) : BEUSCHER et al.

Page 2 of 3

It is certified that error appears in the above-indentified patent and that said Letters Patent is hereby corrected as shown below:

Under the heading "OTHER DOCUMENTS" please insert after the last entry the following:

G. Palu et al., ANTIVIRAL PROPERTIES OF PSORALEN DERIVATIVES: A BIOLOGICAL AND PHYSICO CHEMICAL INVESTIGATION, Biochemical Pharmacology, Vol. 33, No. 21, pp 3451-3456, 1984;

H. Fujita et al., PHOTOBIOLOGICAL ACTIVITIES OF 5-ALKOXYPSORALENS WITH RESPECT TO THE ACTION ON Escherichia coli; Photochemistry and Photobiology, Vol. 43, No. 2, pp. 221-224, 1986

R. Duren et al., QUANTITATIVE STRUCTURE-ACTIVITY RELATIONSHIP OF COUMARIN DERIVATIVES INVOLVEMENT OF PARTITION BETWEEN AQUEOUS AND MEMBRANE PHASE, Journal of Chromatography, Vol. 445, 1988, pp. 49-58

UNITED STATES PATENT AND TRADEMARK OFFICE
CERTIFICATE OF CORRECTION

PATENT NO. : 5,489,585
DATED : February 6, 1996
INVENTOR(S) : BEUSCHER et al.

It is certified that error appears in the above-indentified patent and that said Letters Patent is hereby corrected as shown below:

L. Leenders, PHOTOCHEMISTRY OF NONCONJUGATED BICHROMOPHORIC SYSTEMS CYCLOMERIZATION OF 7,7'-POLYMETHYLENEDIOXYCOUMARINS AND POLYMETHYLENEDICARBOXYLIC ACID (7-COUMARINYL) DIESTERS, J. Org. Chem, Vol. 38, No. 5, 1973, pp. 957-966

K. Muthuramu et al., PHOTODIMERIZATION OF COUMARINS IN MICELLES: LIMITATIONS OF ALIGNMENT EFFECT; J. Org. Chem., 1983, Vol. 48, pp. 1872-1876.

Signed and Sealed this

Sixteenth Day of March, 1999

Attest:

Q. TODD DICKINSON

Attesting Officer

Acting Commissioner of Patents and Trademarks